US008697895B2

(12) United States Patent
Crampton et al.

(10) Patent No.: US 8,697,895 B2
(45) Date of Patent: Apr. 15, 2014

(54) PROCESS FOR PRODUCING AN OXIRANE

(75) Inventors: Hannah L. Crampton, Lake Jackson, TX (US); Philip J. Carlberg, Lake Jackson, TX (US); David H. West, Houston, TX (US); Bruce D. Hook, Lake Jackson, TX (US); William W. Fan, Lake Jackson, TX (US); Anna Forlin, Vigonza (IT)

(73) Assignee: DOW Global Technologies, LLC, Midland, MI (US)

( * ) Notice: Subject to any disclaimer, the term of this patent is extended or adjusted under 35 U.S.C. 154(b) by 121 days.

(21) Appl. No.: 13/388,723

(22) PCT Filed: Aug. 4, 2010

(86) PCT No.: PCT/US2010/044354
§ 371 (c)(1),
(2), (4) Date: Feb. 3, 2012

(87) PCT Pub. No.: WO2011/017401
PCT Pub. Date: Feb. 10, 2011

(65) Prior Publication Data
US 2012/0130095 A1 May 24, 2012

Related U.S. Application Data

(60) Provisional application No. 61/231,414, filed on Aug. 5, 2009.

(51) Int. Cl.
*C07D 301/12* (2006.01)
(52) U.S. Cl.
USPC .......................................................... 549/531
(58) Field of Classification Search
USPC .......................................................... 549/531
See application file for complete search history.

(56) References Cited

U.S. PATENT DOCUMENTS

| 5,262,550 | A | * | 11/1993 | Crocco et al. ................. 549/531 |
| 6,288,248 | B1 |   | 9/2001 | Strebelle et al. |
| 7,323,578 | B2 |   | 1/2008 | Catinat et al. |

FOREIGN PATENT DOCUMENTS

| CN | 1329100 | 10/2008 |
| EP | 0549013 | 6/1993 |
| WO | 02085874 | 10/2002 |
| WO | 2009082536 | 7/2009 |

OTHER PUBLICATIONS

Zhang, et al. "Effects of Organic Solvent Addition on the Epoxidation of Propene Catalyzed by TS-1", Reaction Kinetics and Catalysis Letters, Springer Science+Business Media, Dordrecht, NL, vol. 92, No. 1, Sep. 21, 2007, pp. 49-54.
Pandy, et al. "Eco-Friendly Synthesis of Epichlorohydrin Catalyzed by Titanium Silicate (TS-1) Molecular Sieve and Hydrogen Peroxide", Catalysis Communications, 2007, 8, 379-382.
Clerici, et al. "Epoxidation of Lower Olefins with Hydrogen Peroxide and Titanium Silicalite", Journal of Catalysis, 1993, 140, 71-83.
Li, et al. "Epoxidation of Allyl Chloride to Epichlorohydrin by a Reversible Supported Catalyst with H2O2 Under Solvent-Free Conditions", Organic Process Research & Development, No. 10, 2006, pp. 876-880.
Nur, et al. "Phase-Boundary Catalysis of Alkene Epoxidation with Aqueous Hydrogen Peroxide Using Amphiphilic Zeolite Particles Loaded with Titanium Oxide", Journal of Catalysis, No. 204, 2001, pp. 402-408.
International Search Report and Written Opinion from related PCT application PCT/US2010/044354 dated Dec. 27, 2010, 12 pages.
International Preliminary Report on Patentability from related PCT application PCT/US2010/044354 dated Sep. 26, 2011, 15 pages.
Ullman's Encyclopedia of Industrial Chemistry, 5th edition, vol. A9, "Dithiocarbamic Acid to Ethanol", 1987, pp. 547-563.
Pham, et al., Ullman's Encyclopedia of Industrial Chemistry, vol. 13, "Epoxy Resins", 2012, pp. 155-244.

* cited by examiner

*Primary Examiner* — Taylor Victor Oh
(74) *Attorney, Agent, or Firm* — Brooks, Cameron & Huebsch, PLLC

(57) ABSTRACT

A multiple liquid phase composition and process for preparing an oxirane product, such as epichlorohydrin, including a reaction mixture of: (a) at least one olefin, wherein the olefin is selected from one of (i) an aliphatic olefin or substituted aliphatic olefin, with the proviso that the aliphatic olefin is not propylene, (ii) a cycloaliphatic olefin, (iii) an aromatic olefin, (iv) a cycloaromatic olefin, and (v) mixtures thereof; (b) at least one peroxide compound, (c) at least one catalyst, and (d) and a solvent mixture; wherein the solvent mixture comprises at least (i) at least one alcohol or a combination of alcohols, and (ii) at least one non-reactive co-solvent; wherein the solvents are mixed at a predetermined concentration; wherein the non-reactive co-solvent has a different boiling point than the oxirane product; and wherein the oxirane product partitions into a high affinity solvent during the reaction. The process of the present invention advantageously produces a waste stream with no significant amount of sodium chloride (NaCl). In one embodiment, the present invention includes a process for preparing epichlorohydrin from allyl chloride and hydrogen peroxide including reacting (a) an allyl chloride with (b) hydrogen peroxide, in the presence of (c) a titanium silicalite-1 (TS-1) catalyst and (d) in the presence of a predetermined amount of a mixed solvent system; wherein the mixed solvent system includes at least (i) methanol and (ii) at least one non-reactive co-solvent.

16 Claims, 5 Drawing Sheets

PROCESS FOR PRODUCING AN OXIRANE

This application is a National Stage application under 35 U.S.C. 371 of PCT/US2010/044354, filed on Aug. 4, 2010 and published as WO2011/017401 A1 on Feb. 10, 2011, which claims the benefit of U.S. Provisional Application Ser. No. 61/231,414 filed Aug. 5, 2009, the entire contents of which are incorporated herein by reference in its entirety.

BACKGROUND OF THE INVENTION

1. Field of the Invention

The present invention relates to a process for producing an oxirane, such as epichlorohydrin, by reacting an olefin and a peroxide compound in the presence of a catalyst such as titanium silicalite-1 (TS-1) catalyst and in the presence of a mixed solvent system.

2. Description of Background and Related Art

Oxiranes are valuable chemicals and are useful in a variety of end use applications. Epichlorohydrin, for example, is a valuable chemical commodity used extensively to make epoxy resins on a commercial scale. Currently, a hypochlorous acid (HOCl) process is employed for manufacturing epichlorohydrin. The known process begins with the chlorohydrination of allyl chloride from hypochlorous acid, formed from the reaction of chlorine and water. This known HOCl process forms an isomeric mixture of 1,2- and 1,3-dichlorohydrin, which is subjected to dehydrochlorination in caustic solution to yield epichlorohydrin. The HOCl process is used to make over 95% of epichlorohydrin produced globally, but this known process suffers from the disadvantages of producing high levels of chlorinated organic compounds and salt in waste streams, and of producing large amounts of waste water.

There are several known processes in the art that use peroxide, such as hydrogen peroxide ($H_2O_2$), to produce an oxirane, including for example epichorohydrin, such as the processes disclosed in: Clerici et al., "Epoxidation of Lower Olefins with Hydrogen Peroxide and Titanium Silicalite," Journal of Catalysis, 1993, 140, 71-83; U.S. Pat. No. 7,323, 578; EP Patent Application Publication No. 1993/0549013 A1; Pandey et al., "Eco-friendly Synthesis of Epichlorohydrin Catalyzed by Titanium Silicalite (TS-1) Molecular Sieve and Hydrogen Peroxide," Catalysis Communications, 2007, 8, 379-382; Chinese Patent Application No. CN 200710039080.1; Zhang et al., "Effects of Organic Solvent Addition on the Epoxidation of Propene Catalyzed by TS-1," Reaction Kinetics and Catalysis Letters, 2007, 92(1), 49-54; Li, et al., "Epoxidation of Allyl Chloride to Epichlorohydrin by a Reversible Supported Catalyst with $H_2O_2$ Under Solvent-Free Conditions," Organic Process Research & Development, 2006, 10, 876-880; Patent application PCTUS/08/080, titled "Process for epoxidizing olefins with hydrogen peroxide using supported oxo-diperoxo tungstate catalyst complex"; and U.S. Pat. No. 6,288,248 B1.

For epoxidizing some olefins, such as epichlorohydrin, using a peroxide reaction, it is well known that methanol is a necessary component of the peroxide reaction to obtain high activity. Generally, methanol must be used in large excesses in the known processes. This results in the formation of byproducts from the reaction of methanol and water, which is solubilized in the organic phase by methanol, with an oxirane. It is estimated that the use of these large quantities of methanol would result in the construction of large towers and the consumption of a large amount of energy for the purification of the oxirane product if produced on a commercial scale. Additionally, a titanium silicalite-1 (TS-1) catalyst used under these conditions would deactivate in a matter of hours; and subsequently, would have to be fully regenerated by calcination. Furthermore, the high concentration of methanol promotes the formation of by-products through the reaction of the oxirane product with methanol.

Some of the problems of the known processes described above may be summarized as follows:

(1) The prior art processes use high levels of methanol. The high levels of methanol must be separated from the oxirane product and recycled which creates a high energy use for the process and associated high costs. The high concentrations of methanol also lead to high levels of by-products through solvolysis of the oxirane by methanol.

(2) A heavy solvent is typically added in the prior art processes following the reaction instead of during the reaction. This allows oxirane product to contact and react with components in the reaction mixture such as water and an alcohol phase to form non-usable byproducts. The byproducts decrease the yield of the desired oxirane product; and must be purged from the process.

It is desired to provide a process for preparing an oxirane product that can be operated at reaction conditions that do not have the problems of the above prior art processes; that still maintains a high catalyst activity; that increases the selectivity of the reaction; and that extends the lifetime of the catalyst without the need for any additional components which would have to be removed in a subsequent downstream process.

It is also desired to provide a peroxide process for producing an oxirane product, such as epichlorohydrin, that utilizes a multiphase process instead of a single phase process; and that produces less wastewater than other known processes.

SUMMARY OF THE INVENTION

The problems of the prior art processes may be solved by the process of the present invention which provides a peroxide process for producing an oxirane product, such as epichlorohydrin, for example from allyl chloride and hydrogen peroxide, catalyzed by, for example, titanium silicalite-1 (TS-1), in a mixed solvent system.

The process of the present invention is an attractive alternative for inland sites; and that uses a lower amount of total organic solvent (for example from 230-500 g/kg), and a much lower amount of methanol (for example, less than 100 g/kg) than the prior art processes.

One aspect of the present invention is directed to a multiple liquid phase composition, useful for preparing an oxirane product, comprising a reaction mixture of: (a) at least one olefin, wherein the olefin is selected from one of (i) an aliphatic olefin or substituted aliphatic olefin, with the proviso that the aliphatic olefin is not propylene, (ii) a cycloaliphatic olefin, (iii) an aromatic olefin, (iv) a cycloaromatic olefin, and (v) mixtures thereof; (b) at least one peroxide compound, (c) at least one catalyst, and (d) a solvent mixture; wherein the solvent mixture comprises at least (i) at least one alcohol or a combination of alcohols, and (ii) at least one non-reactive co-solvent; wherein the solvents are mixed at a predetermined concentration; wherein the non-reactive co-solvent has a different boiling point than the oxirane product; and wherein the oxirane product is capable of partitioning into at least one of the solvents present in the solvent mixture during the reaction.

Another aspect of the present invention is directed to a process for preparing the above reaction mixture and an oxirane product from an olefin and a peroxide compound comprising reacting (a) at least one olefin wherein the olefin is selected from one of (i) an aliphatic olefin or substituted aliphatic olefin, with the proviso that the aliphatic olefin is not propylene, (ii) a cycloaliphatic olefin, (iii) an aromatic olefin, (iv) a cycloaromatic olefin, and (v) mixtures thereof; with (b) at least one peroxide compound, in the presence of (c) at least one catalyst and (d) in the presence of a solvent mixture; wherein the solvent mixture comprises at least (i) at least one alcohol or a combination of alcohols at a predetermined concentration and (ii) at least one non-reactive co-solvent at a predetermined concentration; wherein the non-reactive co-solvent has a different boiling point than the oxirane; and wherein the oxirane is capable of partitioning into at least one of the solvents present in the solvent mixture during the reaction.

Still another aspect of the present invention is directed to a process for preparing an oxirane comprising the steps of:

(a) a reacting an olefin wherein the olefin is selected from one of (i) an aliphatic olefin or substituted aliphatic olefin, with the proviso that the aliphatic olefin is not propylene, (ii) a cycloaliphatic olefin, (iii) an aromatic olefin, (iv) a cycloaromatic olefin, and (v) mixtures thereof; a catalyst, a peroxide, an alcohol mixture, and a nonreactive solvent together to form a reaction mixture; wherein the reaction mixture contents comprise at least two liquid phases and a catalyst; and simultaneously decanting the reaction mixture contents; wherein the liquid phases are separated from the catalyst; wherein the liquid phases are recovered for further processing;

(b) separating the two liquid phases of step (a) from each other to form an aqueous phase and an organic phase;

(c) separating, in at least one separation unit operation, organic compounds present in the aqueous phase of step (b), from the aqueous phase to form an organic compounds stream and a wastewater stream;

(d) recycling the organic compounds stream of step (c) to the reaction mixture; and recovering or sending the wastewater stream of step (c) to a subsequent processing operation;

(e) recovering, in at least one operation unit, the organic phase of step (b) comprising the nonreactive solvents, unreacted olefin, and the oxirane;

(f) separating the oxirane from the other components of the organic phase;

(g) recovering the oxirane product from step (f);

(h) recycling the unreacted olefin and the nonreactive solvents stream of step (f) to the reaction mixture; and (i) optionally, purging any undesired compounds which build up in the recycling steps of the process.

The present invention is advantaged because it specifies a multiphase solvent system in which the oxirane produced is preferentially sequestered into the organic phase, reducing its contact with water and thus reducing byproducts resulting from hydrolysis of the oxirane. This both increases the selectivity of the reaction and extends the lifetime of the catalyst without the need for any additional components, which would have to be removed in the downstream process. The multiphasic nature of the reaction mixture also facilitates the subsequent recovery of the oxirane, such as epichlorohydrin, by allowing a simple separation of the aqueous and organic phases by, for example, decantation, prior to recovery of recyclable and useful product components from each stream.

In addition, the present invention is advantaged because the methanol concentrations presented in the present invention are lower than those presented in previously known processes, which decreases losses of oxirane to solvolysis by methanol, therefore increasing the selectivity and maximizing peroxide use.

It has been found that while the present reaction is possible without the presence of methanol or solvent, the catalyst lifetime may be extremely short and may only be regenerated through calcination. The present invention is advantaged because, while the present invention process specifies a multiphase solvent system, the presence of a small amount of methanol, along with a non-reacting cosolvent, causes the oxirane produced to be preferentially sequestered into the organic phase, reducing the contact of the oxirane with water, and thus, reducing byproducts resulting from hydrolysis of the oxirane. This both increases the selectivity of the reaction and extends the lifetime of the catalyst.

BRIEF DESCRIPTION OF THE DRAWINGS

The following drawings illustrate non-limiting embodiments of the present invention, wherein.

DETAILED DESCRIPTION OF THE INVENTION

Figure 1:
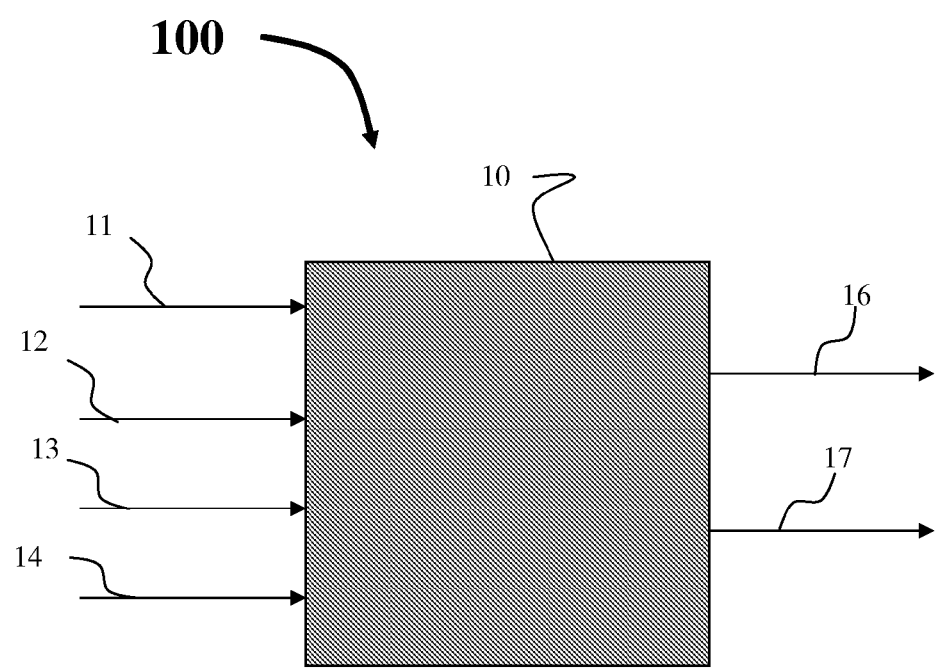
FIG. 1 is a schematic flow diagram showing the overall flows in and out of a reaction/phase separation unit operation for one embodiment of the process of the present invention.

In its broadest scope, the present invention includes a process for preparing an oxirane product from an olefin and a peroxide compound including reacting (a) at least one olefin wherein the olefin is selected from one of (i) an aliphatic olefin or substituted aliphatic olefin, with the proviso that the aliphatic olefin is not propylene, (ii) a cycloaliphatic olefin, (iii) an aromatic olefin, (iv) a cycloaromatic olefin, and (v) mixtures thereof; with (b) at least one peroxide compound, in the presence of (c) at least one catalyst and (d) in the presence of a solvent mixture; wherein the solvent mixture comprises at least (i) at least one alcohol or a combination of alcohols at a predetermined concentration and (ii) at least one non-reactive co-solvent at a predetermined concentration.

The olefin useful in the process of the present invention may comprise acyclic or cyclic aliphatic or aromatic olefins, including those which may contain multiple double bonds, with the proviso that the olefin does not include propylene. The olefins useful in the process of the present invention may include, for example, but are not limited to, other linear alkenes of formula $C_nH_{2n}$, excluding propylene; butadiene and other linear dialkenes of formula $C_nH_{2n-2}$; cyclohexene and other cyclic alkenes and dialkenes; substituted alkenes, such as halogenated alkenes; styrene; divinylbenzene; dicyclopentadiene; and other aromatic alkenes and mixtures thereof. The system of the present invention may also be extended to the oxidation of aliphatic and aromatic alkanes and alcohols, such as, but not limited to, hexane, benzene, hexanol and phenol.

In a preferred embodiment of the present invention, the system may be used to epoxidize allyl chloride to epichlorohydrin using aqueous hydrogen peroxide and titanium silicalite catalyst, TS-1.

The concentration of the at least one olefin is generally between about 10 percent by weight (wt %) to about 90 wt %, preferably between about 20 wt % to about 80 wt %, more preferably between about 30 wt % to about 70 wt %, and most preferably between about 40 wt % to about 65 wt %, based on the total weight of the composition which includes all of the components fed to a reactor to form the reaction mixture including for example the weight all of the liquid components and the catalyst together herein "the total composition."

In one embodiment of the composition and process of the present invention, allyl chloride may be used as the olefin component; and the allyl chloride may be used in a concentration of about 40 wt % to about 65 wt % based on the weight of the total composition.

In the broadest terms of the present invention, "peroxide compound" refers to any molecule containing one or more peroxide (—OO—) functionalities, including organic or inorganic peroxides, peroxide adducts, or peracids. These include, for example, but are not limited to, hydrogen peroxide, urea-hydrogen peroxide adduct, peracetic acid, and mixtures thereof.

The concentration of the peroxide compound may generally be between about 1% to about 35 wt %, preferably between about 1 wt % to about 20 wt %, more preferably between about 1 wt % to about 10 wt %, and most preferably between about 1 wt % to about 7 wt %, based on the weight of the total composition.

One or more peroxides known from the prior art which are suitable for the reaction of the olefin can be used in the present invention. Examples of the peroxides useful in the present invention may include tert-butyl hydroperoxide and ethylbenzene hydroperoxide. In the present invention process, preference is given to using hydrogen peroxide as the peroxide compound. The present invention as described herein, therefore, also provides a process for using hydrogen peroxide as the peroxide compound. Here, preference is given to using an aqueous hydrogen peroxide.

In one preferred embodiment of the present invention, an aqueous solution of hydrogen peroxide at about 30 wt % may be used such that the total amount of molecular hydrogen peroxide may be from about 1 wt % to about 7 wt %, based on the weight of the total composition.

The reaction procedure of the present invention in which the reaction of the oxirane with the hydroperoxide occurs under the pressure and temperature conditions indicated herein, is preferably carried out in the presence of a suitable catalyst.

In the broadest terms of the invention, "catalyst" can be any homogeneous or heterogeneous catalyst appropriate for the epoxidation of an olefin. These may include, but are not limited to, soluble metal catalysts such as ligand-bound rhenium, tungsten, and manganese, and heterogenized forms of these, as well as solid silicate catalysts that preferably contain titanium. These solid catalysts may have the crystal structure of ZSM-5, MCM-22, MCM-41, beta-zeolites, or amorphous titanium on silica.

Preference is given to a heterogeneous catalyst and particularly to a heterogeneous catalyst which comprises a porous oxide material such as zeolite. In general, the catalysts may include, but are not limited to, a titanium-, vanadium-, chromium-, niobium- or zirconium-containing zeolite as the porous oxide material.

Specific examples of suitable zeolites are titanium-, vanadium-, chromium-, niobium- and zirconium-containing zeolites having a pentasil zeolite structure, in particular the types assigned X-ray-crystallographically to the BEA, MOR, TON, MTW, FER, MFI, MEL, CHA, ERI, RHO, GIS, BOG, NON, EMT, HEU, KFI, FAU, DDR, MTT, RUT, RTH, LTL, MAZ, GME, NES, OFF, SGT, EUO, MFS, MWW or mixed MFI/MEL structures and also ITQ-4. It is also possible to use titanium-containing zeolites having the UTD-1, CIT-1 or CIT-5 structure in the process of the present invention. Further titanium-containing zeolites which might be mentioned are those having the ZSM-48 or ZSM-12 structure. Particular preference is given to using Ti zeolites having an MFI, MEL or mixed MFI/MEL structure in the process of the present invention. Further preference is given, specifically, to the, Ti-containing zeolite catalysts which are generally designated as "TS-1", "TS-2" and "TS-3", and also Ti zeolites having a skeletal structure isomorphous with MWW-zeolite.

Particular preference is given to using a heterogeneous catalyst comprising the titanium-containing silicalite TS-1 in the process of the present invention.

It is possible to use the porous oxidic material itself as catalyst in the process of the present invention. However, it is of course also possible to use a shaped body comprising the porous oxidic material as catalyst. The shaped body from the porous oxidic material may be produced using methods well known in the prior art.

The concentration of the catalyst is generally between about 0.1 wt % to about 30 wt %, preferably between about 0.1 wt % to about 20 wt %, more preferably between about 0.1 wt % to about 10 wt %, and most preferably between about 0.5 wt % to about 5 wt %, based on the weight of the total composition.

In a preferred embodiment of the present invention, allyl chloride is converted to epichlorohydrin using hydrogen peroxide and a catalyst such as titanium silicalites with MFI structure (TS-1). In this embodiment the concentration of catalyst may preferably be between about 0.5 wt % to about 5 wt %, based on the weight of the total composition.

The catalyst is typically in solid form in the reaction mixture, while the reaction is carried out in the presence of two liquids, in general an organic phase and an aqueous phase. "Bisphasic" herein means at least two liquid phases. The solid form of the catalyst can be powders for slurry type reactors or extrudates for fixed bed reactors. In one embodiment of the present invention for a slurry reactor system, the catalyst may be mixed with an organic phase, and then the aqueous phase may be added to the mixture to prevent the decomposition of the peroxide. For the slurry reactor system, for example, the size of catalyst may be less than about 100 microns. The amounts of the individual components for the embodiment should be selected based on their physical properties such that when mixed together the liquid composition comprises at least two phases, organic and aqueous.

Component (d) of the present invention is a solvent mixture; wherein the solvent mixture comprises at least (i) at least one alcohol or a combination of two or more alcohols at a predetermined concentration, and (ii) at least one non-reactive co-solvent other than the solvent component (i) at a predetermined concentration; wherein the co-solvent has a different boiling point than the oxirane. The solvent mixture is selected to include at least one solvent having properties such that the oxirane partitions into the at least one solvent present in the solvent mixture during the reaction. The at least one solvent is said to have a high affinity for the oxirane.

"Partitions" herein refers to the tendency of the oxirane product to be more soluble in the solvent mixture phase than in the other phase or phases present in the reaction mixture. It is quantified by the ratio of the oxirane product concentration in the solvent mixture phase to the total amount of oxirane product in the reaction mixture. Generally, the solvent is selected so that 90% or more of the oxirane product in the reaction mixture resides in the solvent phase. Preferably, more than 99% of the oxirane product resides in the solvent phase. Most preferably, 99.9% or more of the oxirane product resides in the solvent phase.

In the broadest scope of the present invention, any alcohol or a mixture of two or more alcohols can be used as the first solvent component of the solvent mixture. The alcohols may include, for example, lower alcohols such as alcohols having less than 6 carbon atoms, for example methanol, ethanol, propanols (e.g. isopropanol), butanols (e.g. tert-butanol) and pentanols and a combination of two or more of these alcohols; halogenated alcohols; and mixtures thereof. Preference is given to using a $C_1$-$C_4$ alcohol (or mixtures thereof), and more specifically to using methanol as the alcohol for the first solvent component. In particular, methanol not only acts as a solvent, but also acts as an activator for the catalyst.

The concentration of the alcohol(s) is generally between about 3 wt % to about 40 wt %, preferably between about 3 wt % to about 20 wt %, more preferably between about 3 wt % to about 10 wt %, and most preferably between about 3 wt % to about 7 wt %, based on the weight of the total composition. In a preferred embodiment of the present invention, methanol may be used at concentrations from about 3 wt % to about 7 wt %, based on the weight of the total composition.

In the broadest terms of the present invention, a "non-reacting or nonreactive co-solvent" is defined as any reagent which is inert to the reaction, i.e. does not take part in the reaction under the reaction conditions, does not react appreciably with peroxide or the product epoxide under reaction conditions, is minimally soluble in water, and has a boiling point substantially different than the oxirane. The criteria of the nonreactive co-solvent having to be "non-reactive" in order to be used in the present invention, may exclude certain reactive compounds such as for example certain olefins, carboxylates, ethers, esters, acyl halides, aldehydes, carbonates, activated aromatics, thiols, amines, molecules containing a nitro-functionality, and certain ketones which are reactive with peroxide, such as acetone and methyl ethyl ketone, for example.

Still solvents which may be used as the non-reactive co-solvent in the present invention may include linear and cyclic alkanes of $C_3$-$C_{18}$, halogenated hydrocarbons, deactivated aromatics, amides, solvents containing nitriles, alcohols, and halogenated alcohols or mixtures thereof. For example, these may include but are not limited to, carbon tetrachloride, propyl chloride, chloroform, dichloromethane, dichloroethane, hexane, octane, decalin, perfluorodecalin, mono- or poly-chlorinated benzenes, mono- or poly-brominated benzenes, acetophenone, benzonitrile, acetonitrile, trichlorotrifluoroethane, trichloroethanol, trifluoroethanol, and tricresyl phosphate or mixtures thereof.

In a particularly advantageous embodiment of the present invention, the non-reacting co-solvent may be selected from those which have solubility parameters similar to the olefin to be epoxidized, as estimated using Hansen parameters and a Teas plot. Preferred non-reacting co-solvents are chosen from, but are not limited to, those with hydrogen bonding force from about 0.0 to about 0.3, dispersion force from about 0.4 to about 1.0, and polar force from about 0.0 to about 0.5. These solvents will have a high affinity for the olefin to be epoxidized, such as epichlorohydrin, and a low affinity for water, resulting in increased sequestration of the olefin to be epoxidized, such as epichlorohydrin, in the organic phase of the multiphase reaction system.

The concentration of the co-solvent is generally between about 5 wt % to about 70 wt %, preferably between about 5 wt % to about 55 wt %, more preferably between about 10 wt % to about 40 wt %, and most preferably between about 10 wt % to about 30 wt %, based on the weight of the total composition.

In a preferred embodiment of the present invention, 1,2-dichlorobenzene may be advantageously used as the non-reacting co-solvent in concentrations between about 10 wt % to about 30 wt %, based on the weight of the total composition.

Other optional components, that may be useful in the present invention, are components normally used in resin formulations known to those skilled in the art. For example, the optional components may comprise compounds that can be added to the composition to enhance the reaction rate, the selectivity of the reaction, and/or the catalyst lifetime. The preferred optional components and their relative concentrations useful in the composition of the present invention can be determined by the skilled artisan.

As an illustration of one embodiment, the present invention may be directed to a specific mixture of a small amount (e.g. 3 wt %-7 wt %) of methanol along with a non-reacting co-solvent, with an excess of an olefin compound, such as allyl chloride, such that the olefin is about 40 wt % to 65 wt %, based on the weight of the total composition, making the olefin such as allyl chloride the main solvent. The resulting reaction mixture consists of at least two liquid phases, the solid catalyst, and a vapor phase which is in contact with the other phases or components present in the reaction mixture, which increases the selectivity of the reaction without the need for other additives.

The reaction of an olefin with a peroxide compound such as hydrogen peroxide for the preparation of an oxirane can be carried out herein by any suitable method, such as for example, in a batch process or continuously. In one embodiment, the process above may be carried out either in at least one batch reactor or at least one continuous reactor, or any combination of these.

With respect to the continuous processes, all suitable reactor arrangements may be useful in the present invention. Thus, for example, the oxirane can be prepared in a cascade of two or more reactors connected to one another in series. Conceivable processes useful in the present invention also include for example those in which reactors are arranged in parallel. Combinations of these processes are also possible. In the case where two or more reactors are connected in series, suitable intermediate treatments can also be provided between the reactors.

For example, in a first embodiment of the process according to the present invention, the olefin, the peroxide, the alcohol(s), the at least one solvent, and the catalyst are fed into at least one reactor, and the resulting liquid phases are removed from the reactor; the catalyst phase in the reactor is separated from the liquid portions of the effluents before the liquid phases are separated. This operation may be carried out in a batch process or continuously. In this first embodiment, any portion of the reactor effluent may be recycled as a feed to the reactor.

In a second embodiment of the process according to the present invention, the olefin, the peroxide, the alcohol(s), the at least one solvent, and the catalyst are fed into at least one reactor, and all of the resulting liquid phases and the catalyst are removed from the reactor and further separated in subsequent operations. This may be carried out in a batch process or continuously. In this second embodiment, any portion of the reactor effluent may be recycled as a feed to the reactor.

In a third embodiment of the process according to the present invention, at least two reactors are connected in series. The olefin, the peroxide, the alcohol(s), the at least one solvent are fed into a first reactor containing catalyst, and the liquid phases are removed from the reactor; the catalyst phase in each reactor is separated from the liquid portions of the effluents before the liquid phases are separated. In this third embodiment, all or a portion of the liquid effluent from the first reactor and subsequent reactor(s) may be fed into a subsequent reactor or reactors containing catalyst, and additionally, fresh olefin, peroxide, alcohol(s), at least one solvent, and catalyst feeds may optionally be added to each subsequent reactor along with the portions of effluent from any previous reactor.

In a fourth embodiment of the process according to the present invention, at least two reactors are connected in series. The olefin, the peroxide, the alcohol(s), and the at least one solvent are fed into the first reactor containing catalyst, and the resulting liquid phases and the catalyst are removed from the first reactor. The catalyst and the liquid phases are separated in subsequent operations. In this fourth embodiment, all or a portion of the liquid effluent and optionally a portion of the catalyst from the first reactor and subsequent reactor(s) may be fed into a subsequent reactor or reactors containing catalyst, and additionally, fresh olefin, peroxide, alcohol(s), at least one solvent, and the catalyst feeds may optionally be added to each subsequent reactor along with the portions of effluent from any previous reactor.

In a fifth embodiment of the process according to the present invention, two or more reactors are operated in parallel. The olefin, the peroxide, the alcohol(s), and the at least one solvent are fed into each reactor containing catalyst, and the resulting liquid phases are removed from each reactor. In this embodiment of the present invention, the catalyst phase in each reactor is separated from the liquid portions of the effluents before the liquid phases are separated. In this fifth embodiment of the invention a portion of the effluent stream from a reactor may be recycled back to that same reactor along with fresh feeds. The reactor effluents may remain separate or may be combined for further processing.

In a sixth embodiment of the process according to the present invention, one or more reactors are operated in parallel. The olefin, the peroxide, the alcohol(s), and the at least one solvent are fed into each reactor containing catalyst, and the resulting liquid phases and the catalyst are removed from each reactor. In this embodiment, a portion of the liquid effluent and, optionally, a portion of the catalyst from each reactor may be recycled back to that same reactor along with fresh feeds. In this sixth embodiment, the reactor effluents may remain separate or may be combined for further processing.

In a seventh embodiment of the process according to the present invention, at least two reactors are connected in series and the olefin and peroxide are fed through the reactors in counter-current flow. The olefin, none or at least a portion of the alcohol(s), the at least one solvent, and the catalyst are fed into the first reactor containing catalyst, and the peroxide and none or at least a portion of the alcohol(s) are fed into the second reactor containing catalyst or, if more than two reactors, into the final reactor. The aqueous phase of the effluent of the final reactor and any reactor downstream of the first reactor, containing partially converted peroxide, is separated from both the catalyst phase and the organic phase containing the oxirane, the at least one solvent, and any remaining olefin, and is fed to one or more upstream reactors in the series. The organic phase of the effluent from the first and subsequent reactor(s), containing any unreacted olefin, alcohol(s), at least one solvent, and oxirane, is separated from both the catalyst phase and the aqueous phase of the effluent and is fed to one or more downstream reactors containing catalyst in the series. This flow pattern repeats for all reactors in the series. In this seventh embodiment of the present invention, the catalyst phase in each reactor is separated from the liquid portions of the effluents before the liquid phases are separated.

In an eighth embodiment of the process according to the present invention, at least two reactors are connected in series and the olefin and peroxide are fed through the reactors in counter-current flow. The olefin, all or a portion of the alcohol(s), the at least one solvent, and the catalyst are fed into the first reactor containing catalyst, and the peroxide and all or a portion of the alcohol(s) are fed into the second reactor or, if more than two reactors, into the final reactor. The aqueous phase of the effluent of the final reactor and any reactor downstream of the first reactor, containing partially converted peroxide, is separated from both the catalyst phase and the organic phase containing the oxirane, the at least one solvent, and any remaining olefin, and is fed to one or more upstream reactors containing catalyst in the series. The organic phase of the effluent from the first and subsequent reactor(s), containing any unreacted olefin, alcohol(s), at least one solvent, and oxirane, is separated from both the catalyst phase and the aqueous phase of the effluent and is fed to one or more downstream reactors containing catalyst in the series. This flow pattern repeats for all reactors in the series. In this eighth embodiment of the present invention, the catalyst phase in each reactor is separated from the liquid portions of the effluents in one or more separate operation(s).

In a ninth embodiment of the process according to the present invention, at least two reactors are connected in series and the olefin and peroxide are fed through the reactors in cross-current flow. The catalyst, the first portion of olefin, a portion of the alcohol(s), the at least one solvent, and all of the peroxide are introduced into a first reactor containing catalyst, an epoxidation of the first portion of the olefin is carried out therein in order to form a first portion of the oxirane. The liquid phases of the effluent of this and subsequent reactor(s) are first separated from the catalyst, and the organic phase of the first reactor containing unreacted olefin, alcohol(s), at least one solvent, and oxirane generated is fed into at least one subsequent reactor containing catalyst, to which fresh peroxide feed is introduced. This flow pattern is repeated for all reactors in the series. The catalyst is separated from the final reactor effluent before the two liquid phases are separated.

In a tenth embodiment of the process according to the present invention, at least two reactors are connected in series and the olefin and peroxide are fed through the reactors in cross-current flow. The first portion of olefin, a portion of the alcohol(s), the at least one solvent, and all of the peroxide are introduced into a first reactor containing catalyst, an epoxidation of the first portion of the olefin is carried out therein in order to form a first portion of the oxirane. The liquid phases of the effluent of this reactor are discharged along with the catalyst, and catalyst is separated from the liquid phases in subsequent operations. The organic phase of the first and subsequent reactor(s) containing unreacted olefin, alcohol(s), at least one solvent, and oxirane generated is fed into at least one subsequent reactor containing catalyst, to which fresh peroxide feed and catalyst are introduced. This flow pattern is repeated for all reactor(s) in the series. The catalyst is separated from the final reactor effluent liquid phases in subsequent operations.

In an eleventh embodiment of the process according to the present invention, at least two reactors are connected in series and the olefin and peroxide are fed through the reactors in cross-current flow. The first portion of olefin, a portion of the alcohol(s), the at least one solvent, and all of the peroxide are introduced into a first reactor containing catalyst, an epoxidation of the first portion of the olefin is carried out therein in order to form a first portion of the oxirane. The liquid phases of the effluent of this reactor are first separated from the catalyst, and the aqueous phase of the first and subsequent reactor(s) containing unreacted peroxide is fed into at least one subsequent reactor containing catalyst, to which fresh olefin, alcohol(s), at least one solvent and catalyst are introduced. This flow pattern is repeated for all reactors in the series. The catalyst is separated from the final reactor effluent before the two liquid phases are separated.

In a twelfth embodiment of the process according to the present invention, at least two reactors are connected in series and the olefin and peroxide are fed through the reactors in cross-current flow. The first portion of olefin, a portion of the alcohol(s), the at least one solvent, and all of the peroxide are introduced into a first reactor containing catalyst, an epoxidation of the first portion of the olefin is carried out therein in order to form a first portion of the oxirane. The liquid phases of the effluent of this reactor are discharged along with the catalyst, and catalyst is separated from the liquid phases in subsequent operations. The aqueous phase of the first and subsequent reactor(s) containing unreacted peroxide is fed into at least one subsequent reactor containing catalyst, to which fresh olefin, alcohol(s), at least one solvent and catalyst are introduced. The catalyst is separated from the final reactor effluent liquid phases in subsequent operations.

The temperature and pressure of the reaction medium can be modified during the process in the course of the preparation of the oxirane from an olefin and a peroxide compound. It is furthermore possible to modify the pressure under which the reaction takes place.

In one preferred embodiment, the process of the present invention produces a waste stream with little, or no significant amount of, sodium chloride (NaCl). By "no significant amount" with reference to the sodium chloride it is meant herein as generally less than about 1 wt %, preferably less than about 0.5 wt %, and most preferably less than about 0.1%, based on the weight of the total composition.

In another embodiment of the process of the present invention, the reaction environment may include a vapor phase in contact with the multiple liquid phase composition. Following the reaction, the resulting two liquid phases formed during the reaction in the reaction mixture, an organic phase and an aqueous phase, may be separated from each other and from the catalyst. Each liquid phase may then be separated into smaller components for recycle, product recovery, or purge stream isolation. Unreacted olefin, alcohol(s), and non-reactive solvent(s) may be returned to the reaction section; and water and byproducts may be purged from the process.

In still another embodiment, the process of the present invention may include immediately separating the water from the reaction product to minimize the contact of these compounds in the high temperature sections of the separation section and thus minimize the formation of by-products.

In a specific embodiment of the present invention, a process for preparing an oxirane includes the steps of:
(a) reacting an olefin, wherein the olefin is selected from one of (i) an aliphatic olefin or substituted aliphatic olefin, with the proviso that the aliphatic olefin is not propylene, (ii) a cycloaliphatic olefin, (iii) an aromatic olefin, (iv) a cycloaromatic olefin, and (v) mixtures thereof; a catalyst, a peroxide compound, an alcohol or a mixture of alcohols, and a nonreactive solvent together to form a reaction mixture; wherein the reaction mixture contents comprise at least two liquid phases and a catalyst; and simultaneously decanting the reaction mixture contents; wherein the liquid phases are separated from the catalyst; and wherein the liquid phases are recovered for further processing;

(b) separating the two liquid phases, recovered from step (a) from each other to form an aqueous phase and an organic phase;

(c) separating, in at least one separation unit operation, organic compounds present in the aqueous phase of step (b), from the aqueous phase to form an organic compounds stream and a wastewater stream;

(d) recycling the organic compounds stream of step (c) to the reaction mixture; and recovering or sending the wastewater stream of step (c) to a subsequent processing operation;

(e) recovering, in at least one operation unit, the organic phase of step (b) comprising the nonreactive solvents, unreacted olefin, and the oxirane;

(f) separating the oxirane from the other components of the organic phase;

(g) recovering the oxirane product from step (f);

(h) recycling the unreacted olefin and the nonreactive solvents stream of step (f) to the reaction mixture; and (i) optionally, purging any undesired compounds which build up in the recycle streams.

Step (a) of the above process may be referred to as a "reaction/decanting step."

In a preferred embodiment, the oxirane, such as epichlorohydrin, may be prepared by a process comprising reacting (a) an olefin, such as allyl chloride, with (b) a peroxide compound, such as hydrogen peroxide, in the presence of (c) a catalyst, such as titanium silicalite-1 (TS-1), and (d) in the presence of a solvent mixture; wherein the solvent mixture comprises at least (i) one or more alcohols, such as methanol, and (ii) at least one non-reacting co-solvent.

In the process of the present invention, the reaction of the olefin such as an allyl chloride with the peroxide compound such as hydrogen peroxide takes place in a reactor which is suitable for this purpose. The preferred starting materials used for the reaction of the present invention process may be fed into the reactor in one or more streams. For example, the streams are fed in liquid form into the reactor to form a multiphasic or at least a biphasic system. In the process of the present invention, preference is given to feeding streams consisting of the combination of the aqueous starting materials and streams consisting of the combination of the organic starting materials into the reactor.

It is possible to use any conceivable reactor known in the art which is best suited for carrying out the respective reaction. In the present invention, the term "reactor" or "reaction vessel" is not restricted to a single vessel. Rather, it is also possible to use a cascade of stirred vessels as the reactor such as described above.

The reaction vessel may comprise any well-known suitable type, including for example, one or more continuous stirred tank reactors (CSTRs) or tubular reactors; or combinations thereof. The reaction vessel may also be a batch reactor. The reactor may comprise any other well known liquid-liquid contactor, such as for example a Karr Column For the reaction step, sufficient mixing may be required to ensure that the olefin, the peroxide compound and the catalyst come into intimate contact. The mixing may comprise any known means for mixing such as for example, but are not limited to, stirring with an agitator, by controlling droplet size in a countercurrent extractor, by inducing shear in with a mixing element in a tubular reactor or loop reactor, or by other means. Mixing intensity should be such that the power/volume input to the reactor is preferably 1 to 100 hp/1000 gal, more preferably 1 to 10 hp/1000 gal and most preferably 2 to 4 hp/1000 gal. Interfacial area needs to be sufficiently high enough to allow sufficient mass transfer to occur for reaction to occur.

Once the catalyst is separated from the liquid reaction phases, the multiple reaction phases facilitate the subsequent recovery of oxirane product, such as epichlorohydrin, by allowing a simple separation of the aqueous and organic phases by, for example, decantation, prior to recovery of recyclable and useful product components from each stream. See for example FIGS. 1-5. By reducing the amount of methanol to a predetermined level, which is lower than the levels used in the prior art processes, the selectivity of the reaction to oxirane product may be increased because the reaction of methanol with oxirane product is reduced. When the methanol is reduced, a reaction mixture of at least two liquid phases results, which is advantageous because the majority of the oxirane product remains in the organic phase, which reduces byproducts, for example 1-chloro-3-methoxy-2 propanol, 1-chloro-2-methoxy-3-propanol, and 1-chloro-2,3-propanediol, formed from the reaction of oxirane product with water and methanol. Also, many of the heavy byproducts formed remain in the aqueous phase. It is a critical element of the reaction that the reaction remains in at least two liquid phases so that the oxirane product formed will be sequestered away from the aqueous phase and into one of the organic phases. This greatly reduces the hydrolysis of the oxirane product to by-products.

The reaction may be carried out in a mixed solvent system consisting of a small amount of methanol with a non-reacting co-solvent. The advantages that the system of the present invention offers are increased catalyst lifetime and decreased energy costs for separation. For example, based on a simulation of the process taught by U.S. Pat. No. 6,288,248 B1 the embodiment presented as FIG. 3 results in a reduction of about 35% in energy required per pound of oxirane product produced. The embodiment presented as FIG. 4 results in a reduction in steam usage and the embodiment presented in FIG. 4 represents an energy reduction of about 55% from the process of the prior art. The presence of methanol in the reactor at a concentration of generally between about 3% to about 40%, preferably between about 3% to about 20%, more preferably between about 3% to about 10%, and most preferably between about 3% to about 7%, based on the weight of the total composition, extends catalyst lifetime as described in the examples.

Another advantage of the present invention is that the addition of the non-reacting co-solvent increases the catalyst lifetime by reducing the plugging of the catalyst pores.

Still another advantage of the present invention is that the biphasic nature of the reaction mixture allows the separation of the organic and aqueous phases by decanting, which reduces the size of distillation towers and the steam consumption, compared to a process that would use a high level of methanol.

It has been discovered that TS-1 catalyst activity in the epoxidation of an olefin such as allyl chloride with a peroxide compound such as $H_2O_2$ can be maintained by using a mixture of solvents comprising less than 10% methanol along with a non-reactive co-solvent. At a temperature of 40° C. and atmospheric pressure, this mixture provides better reuse of the catalyst while also facilitating the separation of oxirane product such as epichlorohydrin from the reaction mix.

The process of the present invention may be carried out at a reaction temperature generally in the range of from about 10° C. to about 100° C., preferably from about 20° C. to about 80° C., and more preferably from about 30° C. to about 50° C. The other conditions of running the process of the present invention, such as pressure would be the relative pressure and other conditions of the reaction associated with the reactor composition at the particular temperature. However, as an illustration, the reaction may be carried out at pressures in the range from 1 bar to 30 bar, preferably from 8 bar to 20 bar and particularly preferably from 8 bar to 15 bar.

The present invention will now be described with reference to the embodiments shown in the Figures wherein FIGS. 1-5 show non-limiting embodiments of the process of the present invention. In addition, FIGS. 1-5 will be described with reference to an example of one embodiment of the present invention comprising the production of epichlorohydrin by reacting an allyl chloride with hydrogen peroxide in the presence of a TS-1 catalyst and a mixed solvent system. In the following descriptions the term "vessel" is defined herein to mean one or more pieces of equipment. "Reaction/decantation vessel" is defined herein to mean any of the embodiments previously described above.

FIG. 1, for example, shows a process of the present invention, generally indicated by the numeral 100, comprising a reaction/decantation vessel 10, wherein an olefin such as an allyl chloride feed stream 11 may be introduced into the reaction/decantation vessel 10. FIG. 1 represents the reaction/decantation steps in the first, third, fifth, seventh, ninth, and eleventh embodiments described above. The reaction/decantation vessel 10 may comprise any well-known suitable type, including for example, one or more continuous stirred tank reactors (CSTRs) or tubular reactors; or combinations thereof, such as for example, described above. The reaction vessel 10 may also comprise a batch reactor.

Also introduced into vessel 10, are a peroxide compound such as hydrogen peroxide feed stream 12, a single or mixed alcohols feed stream 13 containing a minimum amount of methanol, and an inert solvent feed stream 14 containing for example, 1,2-dichlorobenzene. The reaction/decantation vessel 10 contains a solid catalyst, for example a titanium silicalite such as TS-1 which remains within the boundaries of the equipment shown in FIG. 1. Streams 11, 12, 13, and 14 may be introduced into vessel 10 either separately or together. In addition, optionally, all of the streams 11, 12, 13, and 14 may be combined together into one feed stream. Any of the streams 11, 12, 13, or 14 may be introduced at a single point or at multiple points of vessel 10. The relative amounts of streams 11, 12, 13, and 14 are chosen so that when they are combined in vessel 10 a separate aqueous phase exists along with one or more organic phases, the solid catalyst phase, and optionally a vapor phase above the reaction liquids and catalyst.

In vessel 10, allyl chloride may be partially or fully converted to epichlorohydrin with the TS-1 catalyst plus reaction products of epichlorohydrin and methanol, and monochlorohydrin from the hydrolysis of epichlorohydrin. Stream 16 containing for example, primarily water, unreacted hydrogen peroxide, monochlorohydrin, and mixed alcohols may be removed from vessel 10 and may be sent to storage, for further processing such as purification, or to other equipment for further reaction. Stream 17 containing for example, primarily unreacted allyl chloride, epichlorohydrin, a single or mixed alcohols, and nonreactive solvent such as 1,2-dichlorobenzene may be removed from vessel 10 and my be sent to storage, for further processing such as purification, or to other equipment for further reaction.

Figure 2:
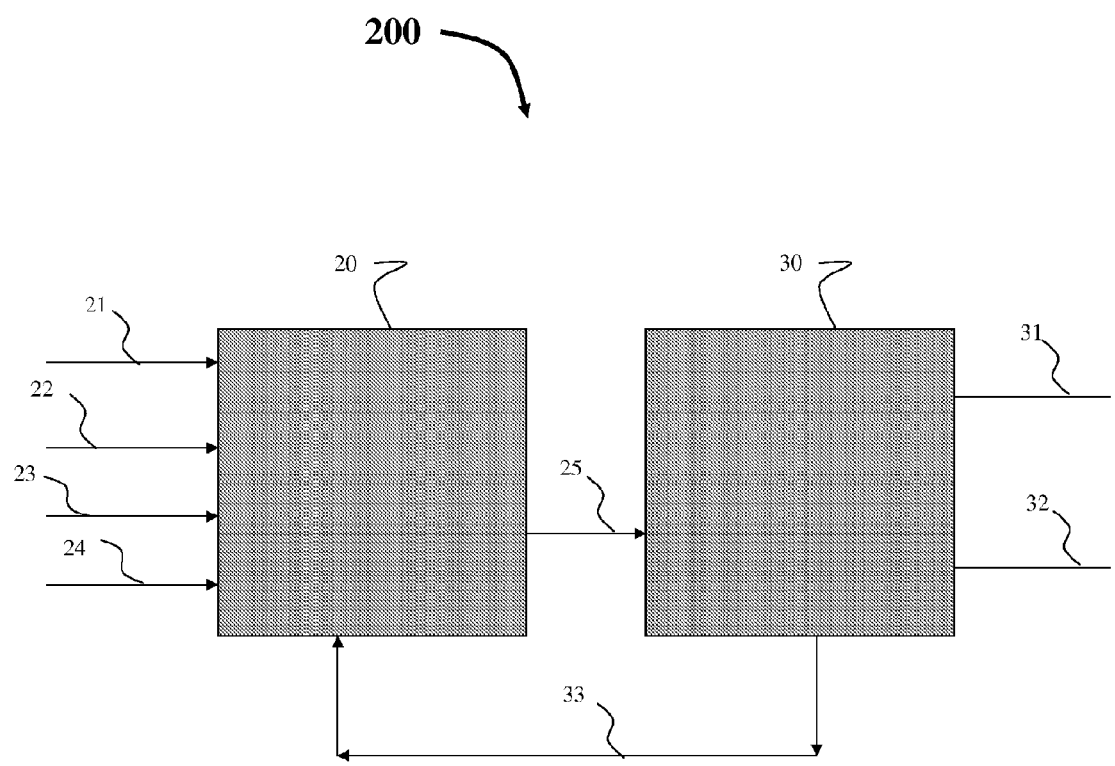
FIG. 2 is a schematic flow diagram showing a reaction unit operation separate from a phase separation unit operation wherein the reaction/phase separation is separate from the product and recycle stream separation section for one embodiment of the process of the present invention.

FIG. 2 shows another embodiment of the process of the present invention generally indicated by numeral 200, wherein an olefin such as an allyl chloride feed stream 21 may be introduced into a reaction vessel 20. FIG. 2 represents the reaction/decantation steps in the second, fourth, sixth, eighth, tenth, and twelfth embodiments described above. The reaction vessel 20 may comprise any well-known suitable type, including for example, one or more continuous stirred tank reactors (CSTRs) or tubular reactors; or combinations thereof, such as for example, as described above. It may also be a batch reactor. Also fed to vessel 20 are a hydrogen peroxide feed stream 22, a single or mixed alcohols feed stream 23 containing a minimum amount of methanol, and an inert solvent feed stream 24 containing for example, 1,2-dichlorobenzene. The reaction vessel 20 contains a solid catalyst 25, for example a titanium silicalite such as TS-1.

Streams 21, 22, 23, and 24, may be introduced into vessel 20 either separately or together. In addition, optionally, all of the streams 21, 22, 23 and 24 may be combined together into one feed stream. Any of the streams 21, 22, 23 or 24 may be introduced at a single point or at multiple points of vessel 20. The relative amounts of streams 21, 22, 23, and 24 are chosen so that when they are combined in vessel 20 a separate aqueous phase exists along with one or more organic phases, the solid catalyst phase, and optionally a vapor phase above the reaction liquids and catalyst.

Also fed to vessel 20 may be a recycle stream 33 comprising mostly solid catalyst, TS-1. Optionally, the solid catalyst may remain in vessel 20 in which case stream 33 would have no flow.

In the embodiment of the current invention shown in FIG. 2 the mixed contents of vessel 20 containing all liquid phases and optionally the solid catalyst may be fed to vessel 30 as stream 26. Vessel 30 may comprise any well-known suitable separation vessel, including decantation, hydrocyclone, mechanically driven high gravity devices, or any suitable known separation apparati known in the art. Stream 31, consisting for example, primarily of water, unreacted hydrogen peroxide, monochlorohydrin, and single or mixed alcohols may be removed from vessel 30 and may be sent to storage, for further processing such as purification, or to other equipment for further reaction. Stream 32, containing for example, primarily unreacted allyl chloride, epichlorohydrin, single or mixed alcohols, and nonreactive solvent such as 1,2-dichlorobenzene may be removed from vessel 30 and may be sent to storage, for further processing such as purification, or to other equipment for further reaction.

Figure 3:
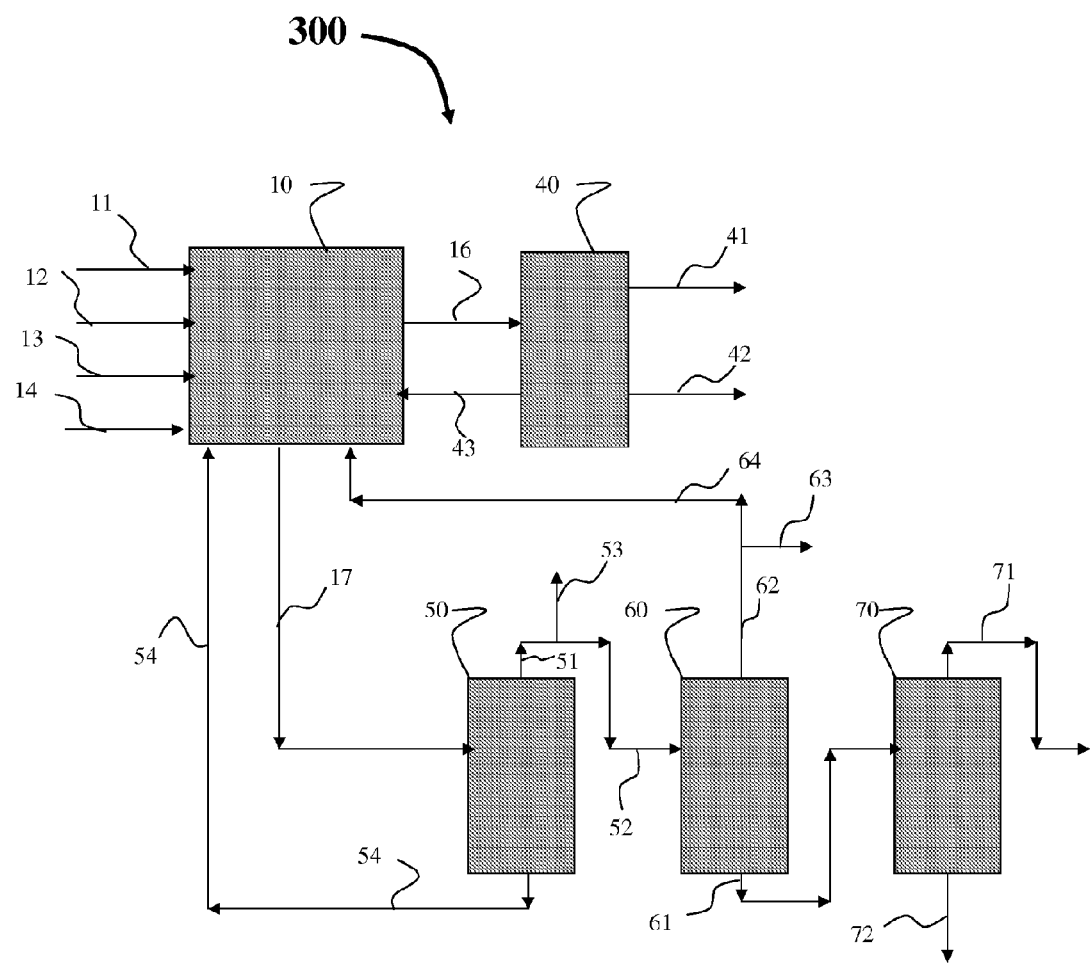
FIG. 3 is a schematic flow diagram showing a reaction/phase separation unit operation and four blocks of unit operations to separate products from byproducts and unreacted reactants following the reaction/phase separation for one embodiment of the process of the present invention.
Figure 4:
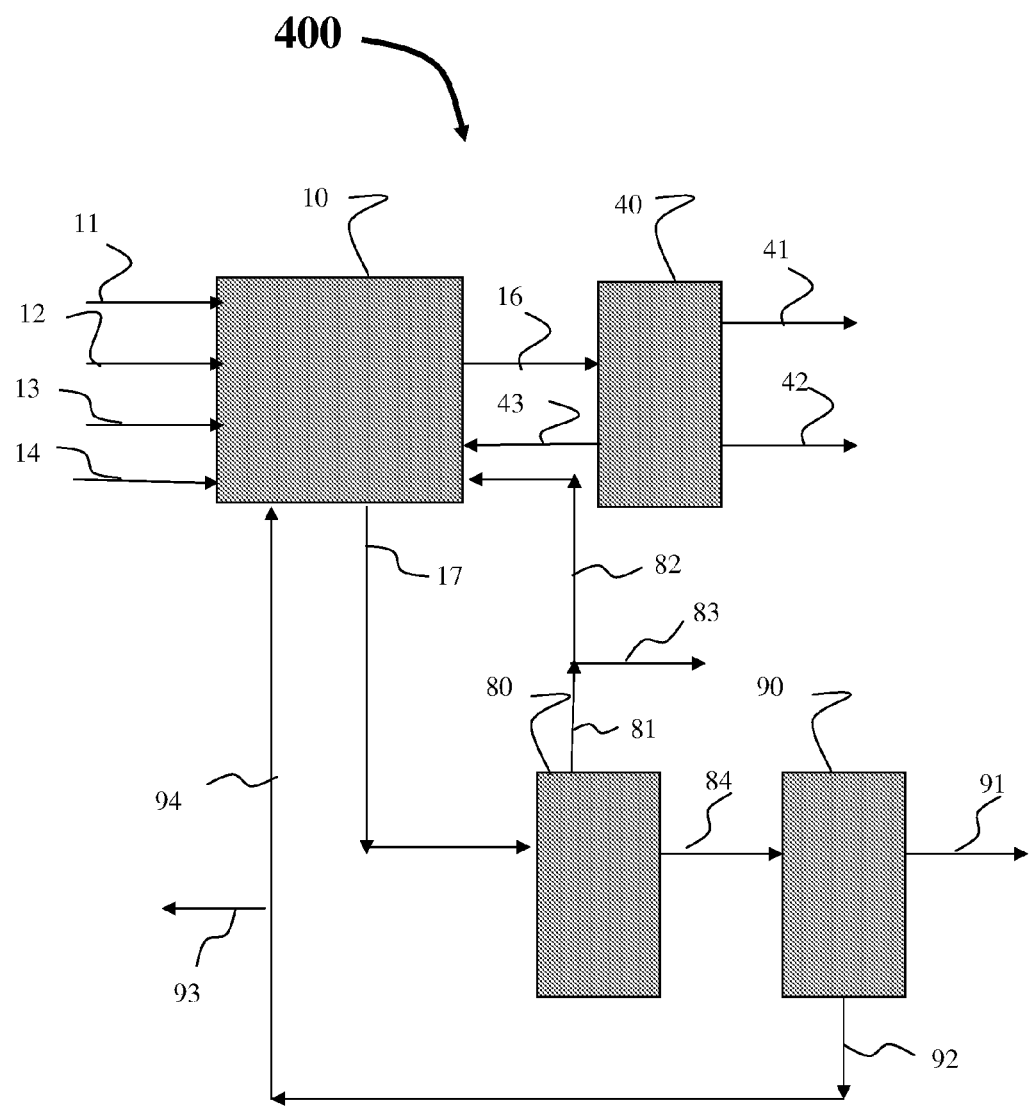
FIG. 4 is a schematic flow diagram showing an embodiment of the present invention with three separation unit operations following reaction/phase separation for one embodiment of the process of the present invention.

FIG. 3 shows another embodiment of the process of the present invention generally indicated by numeral 300, wherein an olefin such as an allyl chloride feed stream, 11, may be introduced into a reaction/decantation vessel 10. The reaction/decantation vessel 10 may comprise any well-known suitable vessel type, including for example, one or more continuous stirred tank reactors (CSTRs) or tubular reactors; or combinations thereof. The vessel 10 may also be a batch reactor. The liquid phases and catalyst may be separated by any well known means of separation such as for example decantation, hydrocyclone, mechanically driven high gravity devices, any suitable known separation apparati, or any combination thereof.

Also introduced into vessel 10 are a hydrogen peroxide feed stream 12 a single or mixed alcohols feed stream 13 containing a minimum amount of methanol 13 and an inert solvent feed stream 14 containing for example, 1,2-dichlorobenzene. The reaction/decantation vessel 10 contains a solid catalyst, for example a titanium silicalite such as TS-1 which remains within the boundaries of the equipment as shown in FIG. 3 as vessel 10. Streams 11, 12, 13, and 14 may be introduced into vessel 10 either separately or together. In addition, optionally, all of the streams 11, 12, 13, and 14 may be combined together into one feed stream. Any of the streams 11, 12, 13, or 14 may be introduced at a single point or at multiple points of vessel 10. The relative amounts of streams 11, 12, 13, and 14 are chosen so that when they are combined in vessel 10 a separate aqueous phase exists along with one or more organic phases, the solid catalyst phase, and optionally a vapor phase above the reaction liquids and catalyst.

In vessel 10, allyl chloride may be partially or fully converted to epichlorohydrin with the TS-1 catalyst, plus reaction products of epichlorohydrin and methanol, and monochlorohydrin from the hydrolysis of epichlorohydrin. Stream 16 containing for example, primarily water, unreacted hydrogen peroxide, monochlorohydrin, and single or mixed alcohols may be removed from vessel 10 and sent to vessel 40 where the mixed alcohols are separated and recycled to vessel 10 as stream 43. Vessel 40 produces stream 42 composed for example, primarily of water and monochlorohydrin and stream 41 composed for example primarily of light feed impurities or by products. Both stream 41 and stream 42 are purged from the process. Stream 17 containing for example, primarily unreacted allyl chloride, epichlorohydrin, single or mixed alcohols, and nonreactive solvent such as 1,2-dichlorobenzene may be removed from vessel 10 and may be sent to vessel 50. Vessel 40 may comprise, for example, a distillation column or a combination of two or more distillation columns.

In vessel 50 the non-reactive solvent, for example 1,2-dichlorobenzene, may be separated and recycled to vessel 10 as stream 54. Stream 51, comprising for example primarily unreacted allyl chloride, mixed alcohols, and epichlorohydrin, exits vessel 50. Optionally, a portion of stream 51 may be removed and purged from the process as stream 53. Stream 52 as the net of stream 51 less any material removed as stream 53 may be fed to vessel 60. Vessel 50 may comprise, for example, a distillation column or a combination of two or more distillation columns.

In vessel 60, the unreacted allyl chloride and single or mixed alcohols are separated and removed from vessel 60 as stream 62. Optionally, a portion of stream 62 may be purged from the process as stream 63. The net of stream 62 less any material removed as stream 63 may be recycled back to vessel 10 as stream 64. Stream 61, comprising for example epichlorohydrin, and compounds with a higher boiling point than epichlorohydrin, may be fed to vessel 70. Vessel 60 may comprise, for example, a distillation column or a combination of two or more distillation columns.

In vessel 70 the product epichlorohydrin may be separated and produced as stream 71. Compounds with boiling points higher than epichlorohydrin are discharged from vessel 70 as stream 72. Vessel 70 may comprise, for example, a distillation column or a combination of two or more distillation columns.

FIG. 4 shows another embodiment of the process of the present invention, generally indicated by numeral 400, wherein an olefin such as an allyl chloride feed stream, 11, may be introduced into a reaction/decantation vessel 10. The reaction/decantation vessel 10 may comprise any well-known suitable type, including for example, one or more continuous stirred tank reactors (CSTRs) or tubular reactors; or combinations thereof. The vessel 10 may also be a batch reactor. The liquid phases and catalyst may be separated by any well known means of separation such as, for example, decantation, hydrocyclone, mechanically driven high gravity devices, any suitable known separation apparati, or any combination thereof.

Also introduced into vessel 10, are a hydrogen peroxide feed stream, 12, a single or mixed alcohols feed stream containing a minimum amount of methanol, 13, and an inert solvent feed stream containing for example, 1,2-dichlorobenzene, 14. The reaction/decantation vessel, 10, contains a solid catalyst, for example a titanium silicalite such as TS-1 which remains within the boundaries of the vessels represented by vessel 10. Streams 12, 13, and 14 may be introduced into vessel 10 either separately or together. In addition, optionally, all of the streams 11, 12, 13, and 14 may be combined together into one feed stream. Any of the streams 11, 12, 13, or 14 may be introduced at a single point or at multiple points of vessel 10. The relative amounts of streams 11, 12, 13, and 14 are chosen so that when they are combined in vessel 10 a separate aqueous phase exists along with one or more organic phases, the solid catalyst phase, and optionally a vapor phase above the reaction liquids and catalyst.

In vessel 10, allyl chloride may be partially or fully converted to epichlorohydrin with the TS-1 catalyst, plus reaction products of epichlorohydrin and methanol, and monochlorohydrin from the hydrolysis of epichlorohydrin. Stream 16, containing for example, primarily water, unreacted hydrogen peroxide, monochlorohydrin, and single or mixed alcohols may be removed from vessel 10 and sent to vessel 10 where the mixed alcohols are separated and recycled to vessel 10 as stream 43. Vessel 40 produces stream 42 composed primarily of water and monochlorohydrin and stream 41 composed primarily of light feed impurities or by products. Both stream 41 and stream 42 are purged from the process. Vessel 40 may comprise, for example, a distillation column or a combination of two or more distillation columns.

In another embodiment, stream 17 containing for example, primarily unreacted allyl chloride, epichlorohydrin, single or mixed alcohols, and nonreactive solvent such as 1,2-dichlorobenzene may be removed from vessel 10 and may be sent to vessel 80 as shown in FIG. 4.

In vessel 80, the unreacted allyl chloride, the single or mixed alcohols, and any organic phase reactor contents with boiling points less than epichlorohydrin are separated as stream 81. A portion of stream 81 my optionally be separated as 83. The net of stream 81 less any removed as stream 83 may be recycled to vessel 10 as stream 82. Stream 84, comprising for example primarily epichlorohydrin, and compounds with boiling points higher than epichlorohydrin, may be fed to vessel 90. Vessel 80 may comprise, for example, a distillation column or a combination of two or more distillation columns.

In vessel 90, the epichlorohydrin product may be separated as stream 91 from the stream 92. Stream 92 may comprise primarily of the nonreactive solvent such as for example 1,2-dichlorobenzene. Optionally, a portion of stream 92 may be removed as stream 93. The net of stream 92 less any removed as stream 93 may be recycled back to vessel 10 as stream 94. Vessel 90 may comprise, for example, a distillation column or a combination of two or more distillation columns.

Figure 5:
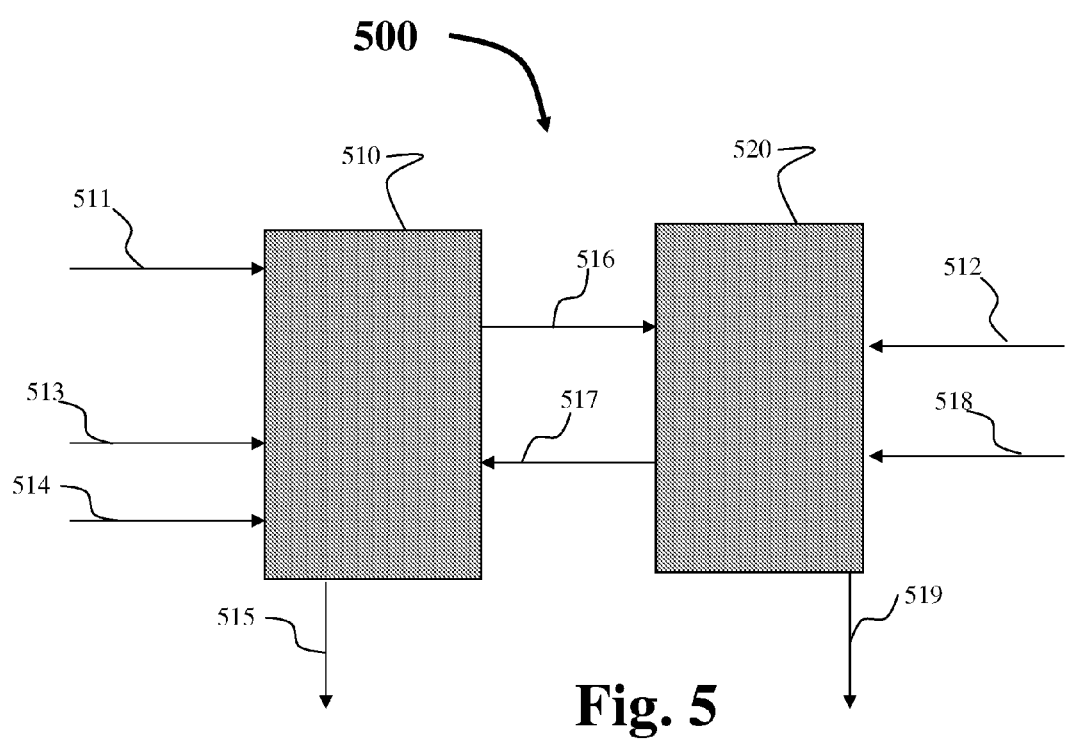
FIG. 5 is a schematic flow diagram of an embodiment of the present invention showing two reactors in series with countercurrent flows.

FIG. 5, shows another embodiment of the process of the present invention, generally indicated by the number 500, comprising two reactors, vessels 510 and 511 connected in series as described above with reference to the seventh embodiment. Feeds are introduced to vessel 510 as an olefin feed stream 511, a single or mixed alcohol stream 513, and an inert solvent feed stream 514. Feeds are introduced to vessel 520 as a peroxide feed stream 512 and a single or mixed alcohol stream 518. The aqueous effluent from vessel 520 as stream 517 is fed to vessel 510. The organic effluent from vessel 510 as stream 516 is fed to vessel 520. The organic phase effluent from vessel 520 is leaves the reactor series as stream 519. The aqueous phase effluent from vessel 510 leaves the reactor series as stream 515.

The oxirane product prepared by the process of the present invention can be used in various applications. In particular, the oxirane, such as epichlorohydrin, produced by the process of the present invention can be used in the production of epoxy resins as described, for example, in Ullman's Encyclopedia of Industrial Chemistry, 5. ed., Vol. A9, pp. 547-562, incorporated herein by reference. Epoxy resins are high performance thermosetting resins which are used, for example, in coatings, electrical laminates, electronic encapsulants, adhesives, and composites.

As an illustration of the present invention, epichlorohydrin produced by the process of the present invention can also be used in the production of synthetic glycerine, elastomers, specialty water treatment chemicals, and wet strength resins for paper production and surfactants.

EXAMPLES

The following examples and comparative examples further illustrate the present invention in detail but are not to be construed to limit the scope thereof.

Some of the various terms and designations used in the following examples include for example, "GC" which stands for "gas chromatography"; and "Epi" which stands for "epichlorohydrin." The allyl chloride used in the Examples was epi-grade, 99.4%, obtained from The Dow Chemical Company. The TS-1 catalyst used in the Examples had a Si/Ti ratio of about 30.

The following standard analytical equipments and methods are used in the Examples:

Gas chromatography was performed on an HP 6890 series G1530A GC with an HP 7682 series injector and FID detection. An HP-1701 14% cyanopropyl phenyl methyl column of length 60.0 m, diameter 320.00 µm, and thickness 1.00 µm was used at temperatures from 35° C. to 250° C.

Peroxide amounts were analyzed by iodometric titration using 0.01N sodium thiosulfate. The peroxide concentration may be calculated as follows: ppm $H_2O_2$=(mL titrant used) (0.01 N)(17000)/g sample. Titrations were performed using a Mettler Toledo DLSx V2.3 titrator with a DM140 sensor.

The reactor used in the following Examples was a 750-mL jacketed glass reactor with a stainless steel cooling coil, thermocouple, mechanical stirrer, addition funnel, $N_2$ purge with gas scrubber, and reflux condenser/cold finger combination.

Example 1 and Example 2

In Example 1, o-dichlorobenzene was used as a non-reacting co-solvent in an epoxidation reaction; and the catalyst from the Example 1 reaction was reused with the same equivalents and reaction conditions in Example 2.

Allyl chloride (247.39 g), TS-1 catalyst (6.946 g), methanol (24.25 g), and o-dichlorobenzene (110.40 g) were added to a reactor. About 30 wt % aqueous hydrogen peroxide (85.34 g) was charged to the addition funnel, and then added to the reactor slowly after the allyl chloride/catalyst/methanol mixture was brought to about 25° C. The mixture was stirred at 600 rpm, and the exothermic reaction raised the temperature up to 40° C., where it was maintained using the cooling coil.

Samples were taken from the reactor by removing an aliquot with a syringe while the stirring was stopped, so that only a portion of the organic phase was removed. The sample was filtered using a 0.45 µm syringe filter to remove any catalyst particles, and then analyzed by gas chromatography (GC).

When the reaction was deemed complete by epi analysis via GC (after 60 minutes), the reactor contents were drained equally into two 250 mL centrifuge tubes, and then centrifuged at 3000 rpm and 0° C. for 30 minutes. The liquid was decanted from the catalyst into a separatory funnel, where the organic and aqueous phases were collected separately. Both phases were analyzed by GC and the amount of peroxide remaining was determined by titration with sodium thiosulfate. The results of these examples are reported in Table II.

Comparative Example A and Comparative Example B

In Comparative Example A an epoxidation reaction with low methanol levels and no non-reacting co-solvent was carried out; and the catalyst from the Comparative Example A reaction was reused with the same equivalents and reaction conditions in Comparative Example B.

The same procedure as described in Example 1 above was used in these examples except that the amount of allyl chloride was 353.77 g, the amount of TS-1 catalyst was 6.924 g, the amount of methanol amount was 24.40 g and no o-dichlorobenzene was used. Also, 30 wt %/aqueous hydrogen peroxide (85.83 g) was used. The reaction was deemed complete by epi analysis via GC after 120 minutes. The results of these examples are reported in Table II.

Comparative Example C and Comparative Example D

In Comparative Example C, an epoxidation reaction was carried out with conditions similar to those in the literature (i.e. higher methanol and no non-reacting co-solvent); and the catalyst from the Comparative Example C reaction was reused with the same equivalents and reaction conditions in Comparative Example D.

The same procedure as described in Example 1 above was used in these examples except that the amount of allyl chloride was 119.55 g, the amount of TS-1 catalyst was 6.881 g, the amount of methanol was 239.07 g, and no o-dichlorobenzene was used. Also, 30 wt %/aqueous hydrogen peroxide (85.21 g) was used. A sample was withdrawn every 15 minutes and filtered using a 0.45 μm syringe filter to remove any catalyst particles, and then analyzed by GC. The reaction was deemed complete by epi analysis via GC after 120 minutes. The results of these examples are reported in Table II.

Comparative Example E and Comparative Example F

In Comparative Example E, an epoxidation reaction was carried out with no methanol and no co-solvent, and the catalyst from the Comparative Example E reaction was reused with the same equivalents and reaction conditions in Comparative Example F except that the reaction time was extended for more conversion.

The same procedure as described in Example 1 above was used in these examples except that allyl chloride (382.0 g) and TS-1 catalyst (6.97 g) were added to a reactor. Also, 30 wt %/aqueous hydrogen peroxide (85.20 g) was used, and the mixture was stirred at 1000 rpm. The reaction was deemed complete by epi analysis via GC after 240 minutes. The results of these examples are reported in Table II.

Example 3 and Example 4

In Example 3, o-dichlorobenzene was used as a non-reacting co-solvent in an epoxidation reaction; and the catalyst from the reaction of Example 3 was reused in Example 4 with the same equivalents and reaction conditions as in Example 3.

The same procedure as described in Example 1 above was used in these examples except that the amount of allyl chloride was 288.00 g, the amount of TS-1 catalyst was 6.909 g, the amount of methanol was 47.06 g, and the amount of o-dichlorobenzene was 43.67 g. Also, 30 wt %/aqueous hydrogen peroxide (85.20 g) was used. The results of these examples are reported in Table II.

Comparative Example G and Comparative Example H

In Comparative Example G, an epoxidation reaction was carried out with the same equivalents and reaction conditions given in Example 1 of Chinese Patent Application No. CN 200710039080.1; and the catalyst from the Comparative Example G reaction was reused with the same conditions in Comparative Example H except that the reaction time was extended for more conversion.

Allyl chloride (400.62 g) and TS-1 catalyst (10.05 g) were added to a reactor. About 30 wt %/aqueous hydrogen peroxide (60.01 g) was charged to the addition funnel, and then added to the reactor slowly after the allyl chloride/catalyst mixture was brought to about 25° C. The mixture was stirred at 1000 rpm, and the exothermic reaction raised the temperature up to 40° C., where it was maintained using the cooling coil.

After 60 minutes the reactor contents were drained equally into two 250 mL centrifuge tubes, and then centrifuged at 3000 rpm and 0° C. for 30 minutes. The liquid was decanted from the catalyst into a separatory funnel, where the organic and aqueous phases were collected separately. Both phases were analyzed by gas chromatography (GC) and the amount of peroxide remaining was determined by titration with sodium thiosulfate. The results of these examples are reported in Table II.

Example 5 and Comparative Example I

In Example 5 and Comparative Example I, reactions of epichlorohydrin and methanol were carried out to demonstrate the advantage of the presence of two liquid phases in the reactor. In Example 5 the reaction of epichlorohydrin and methanol was carried out in the presence of 1,2-dichlorobenzene and water, so that two liquid phases were present. In Comparative Example I, only 1,2-dichlorobenzene, and no water, was used so that only one liquid phase was present.

In Example 5, epichlorohydrin (249.0 g), o-dichlorobenzene (110.0 g), methanol (23.70 g), and water (85.39 g) were added to the reactor and stirred at 40° C. and 600 rpm. After 120 minutes the reactor contents were drained equally into two 250 mL centrifuge tubes, and then centrifuged at 3000 rpm and 0° C. for 30 minutes. The liquid was decanted from the catalyst into a separatory funnel, where the organic and aqueous phases were collected separately. Both phases were analyzed by gas chromatography (GC). The results of this example are reported in Table II.

The same procedure was used in Comparative Example I, except that no water was added. The results of this example are reported in Table II.

Examples 6-13

The same procedure as described in Example 1 above was used in these examples except that the amount of the components were as described in Table I. The results are reported in Table II.

Example 14

The same procedure as described in Example 1 above was used in this example except that that the amounts of the components were as described in Table I. Allyl chloride (161.85 g), dichloromethane (109.7 g), pyrazole (2.05 g), and methyltrioxorhenium catalyst (0.3191 g) were added to a reactor. Also, 30 wt %/aqueous hydrogen peroxide (59.98 g) was charged to the addition funnel, and then added to the reactor slowly after the allyl chloride/catalyst/methanol mixture was cooled to about 9° C. The reaction was deemed complete by epi analysis via GC after 300 minutes. The organic layer was washed with two 250 mL portions of 0.1N sodium thiosulfate and then with two 250 mL portions of water. The organic layer was analyzed by GC and the amount of peroxide remaining in the aqueous layer was determined by titration with sodium thiosulfate. The results of this example are reported in Table II.

TABLE I

| | Components | | | | | |
|---|---|---|---|---|---|---|
| Example | Allyl Chloride (g) | TS-1 Catalyst (g) | Methanol (MeOH) (g) | o-DCB (g) | 30 wt %/ aqueous H2O2 (g) | Reaction Complete GC Analysis (minutes) |
| 1 | 247.39 | 6.946 | 24.25 | 110.40 | 85.34 | |
| 2 | 247.39 | 6.946 | 24.25 | 110.40 | 85.34 | |
| Comp. A | 353.77 | 6.924 | 24.40 | none | 85.83 | 120 |
| Comp. B | 353.77 | 6.924 | 24.40 | none | 85.83 | 120 |
| Comp. C | 119.55 | 6.881 | 239.07 | none | 85.21 | 120 |
| Comp. D | 119.55 | 6.881 | 239.07 | none | 85.21 | 120 |
| Comp. E | 382.0 | 6.97 | | none | 85.20 | 240 |
| Comp. F | 382.0 | 6.97 | | none | 85.20 | 240 |
| 3 | 288.00 | 6.909 | 47.06 | 43.67 | 85.20 | |
| 4 | 288.00 | 6.909 | 47.06 | 43.67 | 85.20 | |
| Comp. G | 400.62 | 10.05 | | none | 60.01 | |
| Comp. H | 400.62 | 10.05 | | none | 60.01 | |
| 5 | Epichlorohydrin 249.0 | | 23.70 | 110.0 | Water 85.39 | |
| Comp. I | Epichlorohydrin 249.0 | | 23.70 | 110.0 | No Water | |
| 6 | 244.95 | 10.507 | 24.09 | 112.77 | 85.81 | |
| 7 | 242.11 | 13.815 | 24.20 | 110.1 | 85.22 | |
| 8 | 290.80 | 6.94 | 23.76 | 110.85 | 42.87 | 180 |
| 9 | 247.74 | 6.884 | 25.35 | 110.81 | 127.73 | 120 |
| 10 | 248.21 | 6.906 | 23.71 | 112.40 | 51.12 (50 wt %) | |
| 11 | 1-Octene(1) 247.97 | 6.931 | 24.53 | 110.15 | 85.38 | |
| 12 | Styrene(2) 250.95 | 6.9414 | 24.30 | 110.48 | 85.66 | 240 |
| 13 | Allyl alcohol 247.9 | 6.948 | 24.15 | 110.45 | 85.32 | 240 |
| 14 | 161.85 | Methyltrioxo rhenium 0.3191 | Pyrazole 2.05 | DCM 109.7 | 59.98 | 300 |

Notes for Table I:
(1)1-octene was used instead of allyl chloride
(2)styrene was used instead of allyl chloride In the above Table I and the following Table II, "o-DCB" stands for 1,2-dichlorobenzene. In Table II, "CMP" stands for 1-chloro, 3-methoxy, 2-propanol; "MCH" stands for 1-chloro-2,3-propanediol (monochlorohydrin); "epi" stands for epichlorohydrin; and "DCM" stands for dichloromethane.

In Table II, "Yield" is calculated as (the amount of epi produced)/(theoretical amount of epi if all $H_2O_2$ added was converted to epi); "$H_2O_2$ conversion" is calculated as (the total peroxide consumed during the reaction)/(peroxide added to the reaction); and "Selectivity" is calculated as (the amount of $H_2O_2$ converted to epi)/(the amount of $H_2O_2$ consumed during the reaction).

Table II is a summary of the results of the above experiments in the Examples and the Comparative Examples. The benefit of reducing the methanol (Comparative Example A and Comparative Example B) without adding a cosolvent versus higher methanol without a cosolvent (Comparative Example C and Comparative Example D) is demonstrated by lower amounts of CMP on the first use and reuse of the catalyst. The benefits of a co-solvent (Examples 1 and 2) versus no co-solvent (Comparative Example A. and Comparative Example B.) are demonstrated by shorter reaction time, higher yields, and higher selectivities on both the first use of the catalyst and on the reuse. The benefits of a co-solvent (Examples 1 and 2) versus high methanol conditions similar to the literature (Comparative Example C and Comparative Example D) are demonstrated by higher yields, higher selectivities, and more particularly, much lower amounts of CMP on both the first use of the catalyst and the reuse. The benefits of using an alcohol/co-solvent mixture (Examples 1 and 2) versus no solvent at all (Comparative Example G and Comparative Example H), as described in Chinese Patent Application No. CN 200710039080.1 is demonstrated by shorter reaction times, higher yields and selectivities, and in particular, much lower amounts of MCH. Comparative Example G and Comparative Example H demonstrate that the reaction conditions claimed in Chinese Patent Application No. CN 200710039080.1 does not lead to satisfactory reuse of the catalyst.

Example 5 and Comparative Example I demonstrate a further advantage of this invention, specifically the utility of the formation of multiple liquid phases in the inhibition of formation of the CMP byproduct. In Example 5 and Comparative Example I, the amounts of epichlorohydrin, methanol, and catalyst are equal. The only difference is the presence or absence of water, and therefore the existence of either one or two liquid phases. The existence of the system as two liquid phases significantly suppresses the formation of CMP.

Examples 6-10 demonstrate preferred embodiments of the present invention and are meant to show the utility of the invention over different reagent concentrations. Examples 11-13 demonstrate other embodiments of the present invention, showing the versatility of the invention in the epoxidation of several different olefins. Example 14 demonstrates the utility of the present invention with a homogeneous catalyst.

TABLE II

Results

| Example | Co-solvent | MeOH wt. % | Reaction Time (minutes) | Yield | $H_2O_2$ conversion | Selectivity | CMP/epi (wt.) | MCH/epi (wt.) |
|---|---|---|---|---|---|---|---|---|
| 1 | o-DCB | 5% | 60 | 94.0% | 99.3% | 94.7% | 0.012 | 0.004 |
| 2 | o-DCB | 5% | 120 | 93.1% | 99.2% | 93.8% | 0.016 | 0.005 |
| Comp. A | None | 5% | 120 | 90.9% | 99.5% | 91.4% | 0.012 | 0.002 |
| Comp. B | None | 5% | 180 | 86.6% | 99.2% | 87.3% | 0.019 | 0.007 |
| Comp. C | None | 53% | 120 | 93.7% | 99.7% | 94.0% | 0.029 | 0.005 |
| Comp. D | None | 53% | 180 | 91.8% | 97.8% | 93.9% | 0.032 | 0.005 |
| Comp. E | None | — | 240 | 85.0% | 92.4% | 92.1% | 0.000 | 0.120 |
| Comp. F | None | — | 300 | 44.8% | 84.0% | 53.3% | 0.000 | 0.226 |
| 3 | o-DCB | 10% | 60 | 90.2% | 99.7% | 90.4% | 0.002 | 0.001 |
| 4 | o-DCB | 10% | 120 | 90.3% | 99.6% | 90.7% | 0.015 | 0.003 |
| Comp. G | None | 0% | 60 | 77.2% | 94.5% | 81.7% | 0.000 | 0.105 |
| Comp. H | None | 0% | 240 | 75.6% | 96.2% | 78.6% | 0.000 | 0.097 |
| 5 | o-DCB | 5% | 120 | — | — | — | 0.005 | 0.002 |
| Comp. I | o-DCB | 5% | 120 | — | — | — | 0.014 | 0.000 |
| 6 | o-DCB | 5% | 60 | 92.1% | 99.5% | 92.5% | 0.016 | 0.006 |
| 7 | o-DCB | 5% | 60 | 92.3% | 99.4% | 92.8% | 0.021 | 0.009 |
| 8 | o-DCB | 5% | 180 | 84.5% | 97.7% | 86.5% | 0.017 | 0.003 |
| 9 | o-DCB | 5% | 120 | 88.1% | 95.3% | 92.4% | 0.021 | 0.020 |
| 10 | o-DCB | 5% | 60 | 91.4% | 97.5% | 93.7% | 0.009 | 0.002 |
| 11 | o-DCB | 5% | 180 | 7.6% | 71.8% | 10.7% | — | — |
| 12 | o-DCB | 5% | 240 | 2.1% | 31.5% | 8.6% | — | — |
| 13 | o-DCB | 5% | 240 | 89.4% | 97.0% | 92.2% | — | — |
| 14 | DCM | — | 300 | 2.0% | 9.7% | 20.5% | — | — |

The invention claimed is:

1. A multiple liquid phase composition, useful for preparing an oxirane product, comprising a reaction mixture of: (a) at least one olefin; wherein the olefin is selected from one of (i) an aliphatic olefin or substituted aliphatic olefin, with the proviso that the aliphatic olefin is not propylene, (ii) a cycloaliphatic olefin, (iii) an aromatic olefin, (iv) a cycloaromatic olefin, and (v) mixtures thereof; (b) at least one peroxide compound, (c) at least one catalyst selected from the group consisting of a titanium silicate catalyst, a ZSM-5 catalyst, a MCM-22 catalyst, a MCM-41 catalyst, beta-zeolites or a combination thereof, and (d) a solvent mixture; wherein the solvent mixture comprises (i) at least one alcohol, and (ii) 1,2-dichlorobenzene; wherein the at least one alcohol and the 1,2-dichlorobenzene are mixed at a predetermined concentration such that the at least one alcohol is from about 3 weight percent to about 40 weight percent based on a weight of the total composition and the 1,2-dichlorobenzene is from about 5 weight percent to about 70 weight percent based on the weight of the total composition; wherein the 1,2-dichlorobenzene has a different boiling point than the olefin and the oxirane product; and wherein the oxirane product is capable of partitioning into at least one of the solvents present in the solvent mixture during the reaction.

2. The composition of claim 1, wherein the at least one olefin comprises allyl chloride; and the at least one oxirane product comprises epichlorohydrin.

3. The composition of claim 1, wherein the at least one peroxide compound comprises hydrogen peroxide.

4. The composition of claim 1, wherein the at least one alcohol of the solvent mixture comprises C1 to C4 alcohol.

5. The composition of claim 1, wherein the at least one alcohol of the solvent mixture comprises methanol.

6. The composition of claim 5, wherein the concentration of the methanol comprises from about 3 weight percent to about 40 weight percent.

7. A multiple liquid phase process for preparing an oxirane product from an olefin and a peroxide compound comprising reacting (a) at least one olefin wherein the olefin is selected from one of (i) an aliphatic olefin or substituted aliphatic olefin, with the proviso that the aliphatic olefin is not propylene, (ii) a cycloaliphatic olefin, (iii) an aromatic olefin, (iv) a cycloaromatic olefin, and (v) mixtures thereof; with (b) at least one peroxide compound, in the presence of (c) at least one catalyst selected from the group consisting of a titanium silicate catalyst, a ZSM-5 catalyst, a MCM-22 catalyst, a MCM-41 catalyst, beta-zeolites or a combination thereof, and (d) in the presence of a solvent mixture; wherein the solvent mixture comprises at least (i) at least one alcohol or a combination of alcohols at a predetermined concentration and (ii) 1,2-dichlorobenzene at a predetermined concentration such that the at least one alcohol or the combination of alcohols is from about 3 weight percent to about 40 weight percent based on a weight of the total composition and 1,2-dichlorobenzene is from about 5 weight percent to about 70 weight percent based on the weight of the total composition; wherein the 1,2-dichlorobenzene has a different boiling point than the olefin and the oxirane; and wherein the oxirane partitions into a high affinity solvent during the reaction.

8. The process of claim 7, wherein the process produces a waste stream with an amount sodium chloride (NaCl) of less than about 0.1 weight percent.

9. The process of claim 7, wherein the oxirane product is epichlorohydrin (a) the at least one olefin is allyl chloride, (b) the at least one peroxide compound is hydrogen peroxide, (c) the at least one catalyst is a titanium silicalite-1 (TS-1) catalyst and (i) the at least one alcohol is methanol as a first solvent and (ii) the 1,2-dichlorobenzene is a second solvent.

10. A process for preparing an oxirane comprising the steps of:

(a) reacting an olefin, wherein the olefin is selected from one of (i) an aliphatic olefin or substituted aliphatic olefin, with the proviso that the aliphatic olefin is not propylene, (ii) a cycloaliphatic olefin, (iii) an aromatic olefin, (iv) a cycloaromatic olefin, and (v) mixtures thereof; a catalyst selected from the group consisting of a titanium silicate catalyst, a ZSM-5 catalyst, a MCM-22 catalyst, a MCM-41 catalyst, beta-zeolites or a combination thereof, a hydrogen peroxide, an alcohol mixture, and 1,2-dichlorobenzene together to form a reaction mixture such that the alcohol mixture is from about 3 weight percent to about 40 weight percent based on a weight of the total reaction mixture and the 1,2-dichlorobenzene is from about 5 weight percent to about 70 weight percent based on the weight of the total reaction mixture; wherein the reaction mixture contents comprise at least two liquid phases and a catalyst; and simultaneously decanting the reaction mixture contents; wherein the liquid phases are separated from the catalyst; wherein the liquid phases are recovered for further processing;

(b) separating the two liquid phases of step (a) from each other to form an aqueous phase and an organic phase;

(c) separating, in at least one separation unit operation, organic compounds present in the aqueous phase of step (b), from the aqueous phase to form an organic compounds stream and a wastewater stream;

(d) recycling the organic compounds stream of step (c) to the reaction mixture; and recovering or sending the wastewater stream of step (c) to a subsequent processing operation;

(e) recovering, in at least one operation unit, the organic phase of step (b) comprising the 1,2-dichlorobenzene, unreacted olefin, and the oxirane;

(f) separating the oxirane from the other components of the organic phase;

(g) recovering the oxirane product from step (f);

(h) recycling the unreacted olefin and the 1,2-dichlorobenzene stream of step (f) to the reaction mixture; and (i) optionally, purging any undesired compounds which build up in the recycling steps of the process.

11. The process of claim 10, wherein the at least one olefin comprises allyl chloride; wherein the at least one peroxide compound comprises hydrogen peroxide; wherein the at least one catalyst comprises a titanium silicate catalyst; and wherein the at least one alcohol of the solvent mixture comprises methanol.

12. The process of claim 10, wherein the reaction step is carried out in at least 2 reactors connected in series and wherein the olefin and peroxide streams are fed through the reactors in counter-current flow, in co-current flow or in cross-current flow.

13. The process of claim 12 wherein the catalyst and liquid phases are separated in a subsequent operation.

14. The process of claim 7, wherein the at least one olefin comprises allyl chloride; wherein the at least one peroxide compound comprises hydrogen peroxide; wherein the at least one catalyst comprises a titanium silicate catalyst; and wherein the at least one alcohol of the solvent mixture comprises methanol.

15. The process of claim 7, wherein the reaction step is carried out in at least 2 reactors connected in series and wherein the olefin and peroxide streams are fed through the reactors in counter-current flow, in co-current flow or in cross-current flow.

16. The process of claim 15 wherein the catalyst and liquid phases are separated in a subsequent operation.

* * * * *

UNITED STATES PATENT AND TRADEMARK OFFICE
CERTIFICATE OF CORRECTION

PATENT NO. : 8,697,895 B2  
APPLICATION NO. : 13/388723  
DATED : April 15, 2014  
INVENTOR(S) : Hannah L. Crampton et al.

It is certified that error appears in the above-identified patent and that said Letters Patent is hereby corrected as shown below:

On the Title page, item (73) Assignee "DOW Global Technologies, LLC" should read "Dow Global Technologies LLC"

Signed and Sealed this  
Fifth Day of May, 2015

Michelle K. Lee  
*Director of the United States Patent and Trademark Office*